(12) United States Patent
Gardner, Jr. et al.

(10) Patent No.: US 8,379,193 B2
(45) Date of Patent: Feb. 19, 2013

(54) SWIR TARGETED AGILE RAMAN (STAR) SYSTEM FOR ON-THE-MOVE DETECTION OF EMPLACE EXPLOSIVES

(75) Inventors: Charles W. Gardner, Jr., Gibsonia, PA (US); Matthew Nelson, Harrison City, PA (US)

(73) Assignee: ChemImage Corporation, Pittsburgh, PA (US)

( * ) Notice: Subject to any disclaimer, the term of this patent is extended or adjusted under 35 U.S.C. 154(b) by 356 days.

(21) Appl. No.: 12/802,994

(22) Filed: Jun. 17, 2010

(65) Prior Publication Data

US 2012/0147358 A1 Jun. 14, 2012

Related U.S. Application Data

(63) Continuation-in-part of application No. 12/199,145, filed on Aug. 27, 2008, now Pat. No. 8,054,454, and a continuation-in-part of application No. 12/754,229, filed on Apr. 5, 2010.

(60) Provisional (Continued)

(51) Int. Cl.
*G01N 21/00* (2006.01)
(52) U.S. Cl. .............................. 356/73; 356/301; 250/332
(58) Field of Classification Search .................. 356/301, 356/72–73; 250/332
See application file for complete search history.

(56) References Cited

U.S. PATENT DOCUMENTS

| | | | |
|---|---|---|---|
| 4,560,275 A * | 12/1985 | Goetz | ........................... 356/326 |
| 5,196,682 A | 3/1993 | Englehardt | |
| 5,216,484 A | 6/1993 | Chao et al. | |
| 5,394,237 A * | 2/1995 | Chang et al. | .................. 356/328 |
| 6,006,140 A | 12/1999 | Carter | |
| 6,244,535 B1 | 6/2001 | Felix | |
| 6,274,871 B1 | 8/2001 | Dukor et al. | |
| 6,422,508 B1 | 7/2002 | Barnes | |
| 6,477,907 B1 | 11/2002 | Chambers | |
| 6,606,566 B1 | 8/2003 | Sunshine | |
| 6,658,915 B2 | 12/2003 | Sunshibne | |
| 6,820,012 B2 | 11/2004 | Sunshine | |
| 6,844,817 B2 | 1/2005 | Gleine | |
| 6,967,612 B1 | 11/2005 | Gorman | |

(Continued)

FOREIGN PATENT DOCUMENTS

| | | |
|---|---|---|
| EP | 2083259 | 7/2009 |
| WO | WO/91/08466 | 6/1991 |

(Continued)

OTHER PUBLICATIONS

Sharma, et al, "Stand-Off Raman Spectroscopic Detection of Minerals on Planetary Surfaces", Hawaii Institute of Geophysics and Planetology, pp. 2391-2407, 2003.

(Continued)

*Primary Examiner* — Kara E Geisel

(57) ABSTRACT

The present disclosure provides for a system and method for detecting explosives and other materials in a sample scene. First interacted photons are produced from a target area wherein the first interacted photons are generated via solar radiation. The first interacted photons are assessed to thereby generate a SWIR hyperspectral image. The SWIR hyperspectral image is analyzed to identify an area of interest likely of comprising an explosive material. The area of interest is illuminated using laser light illumination to generate second interacted photons from the area of interest. These second interacted photons are assessed to determine whether it not an explosive material is present in the area of interest. The system and method may be configured in standoff, OTM, static and UGV configurations.

34 Claims, 13 Drawing Sheets

Related U.S. Application Data application No. 61/268,885, filed on Jun. 17, 2009, provisional application No. 61/278,393, filed on Oct. 6, 2009, provisional application No. 61/335,785, filed on Jan. 12, 2010, provisional application No. 61/301,814, filed on Feb. 5, 2010, provisional application No. 61/395,440, filed on May 13, 2010, provisional application No. 61/324,963, filed on Apr. 16, 2010, provisional application No. 61/305,667, filed on Feb. 18, 2010.

(56) References Cited

U.S. PATENT DOCUMENTS

| | | |
|---|---|---|
| 6,985,216 B2 | 1/2006 | Treado |
| 6,985,233 B2 | 1/2006 | Tuschel |
| 7,012,695 B2 | 3/2006 | Maier |
| 7,084,972 B2 | 8/2006 | Treado |
| 7,088,435 B2 | 8/2006 | Brestel et al. |
| 7,164,117 B2 | 1/2007 | Breed |
| 7,239,974 B2 | 7/2007 | Gulati |
| 7,246,613 B1 | 7/2007 | Mohar |
| 7,262,839 B2 | 8/2007 | Treado |
| 7,277,178 B2 | 10/2007 | Shpantzer |
| 7,286,222 B2 | 10/2007 | Gardner, Jr. |
| 7,295,308 B1 | 11/2007 | Samuels |
| 7,307,705 B2 | 12/2007 | Treado |
| 7,322,267 B1 | 1/2008 | Munson |
| 7,386,372 B2 | 6/2008 | Breed |
| 7,417,727 B2 | 8/2008 | Polonskiy |
| 7,420,664 B2 | 9/2008 | Treado et al. |
| 7,420,675 B2 | 9/2008 | Giakos |
| 7,440,096 B2 | 10/2008 | Gardner |
| 7,486,395 B2 | 2/2009 | Treado |
| 7,502,118 B2 | 3/2009 | Shpantzer |
| 7,511,624 B2 | 3/2009 | Shaw |
| 7,525,102 B1 | 4/2009 | Henshaw |
| 7,542,138 B2 | 6/2009 | Gardner |
| 7,548,310 B2 | 6/2009 | Gardner |
| 7,551,715 B2 | 6/2009 | Rothschild |
| 7,573,570 B2 | 8/2009 | Zhang |
| 7,596,242 B2 | 9/2009 | Breed |
| 7,644,606 B2 | 1/2010 | Sheen |
| 7,663,502 B2 | 2/2010 | Breed |
| 7,676,062 B2 | 3/2010 | Breed |
| 7,687,276 B2 | 3/2010 | Kunz |
| 7,692,775 B2 | 4/2010 | Treado et al. |
| 2001/0052979 A1 | 12/2001 | Treado et al. |
| 2003/0058112 A1 | 3/2003 | Gleine |
| 2003/0123056 A1 | 7/2003 | Barnes |
| 2003/0216869 A1 | 11/2003 | Sunshine |
| 2004/0051867 A1 | 3/2004 | Brestel |
| 2004/0191859 A1 | 9/2004 | Tabacco |
| 2005/0030533 A1 | 2/2005 | Treado |
| 2005/0030545 A1 | 2/2005 | Tuschel |
| 2005/0030657 A1 | 2/2005 | Maier |
| 2005/0041244 A1 | 2/2005 | Treado |
| 2005/0079626 A1 | 4/2005 | Kunz |
| 2005/0105099 A1 | 5/2005 | Shpantzer |
| 2005/0264813 A1 | 12/2005 | Giakos |
| 2006/0007437 A1 | 1/2006 | Treado |
| 2006/0021498 A1 | 2/2006 | Moroz |
| 2006/0146315 A1 | 7/2006 | Treado |
| 2006/0167595 A1 | 7/2006 | Breed et al. |
| 2006/0170922 A1 | 8/2006 | Wang et al. |
| 2006/0203238 A1 | 9/2006 | Gardner, Jr. et al. |
| 2006/0208169 A1 | 9/2006 | Breed et al. |
| 2006/0209301 A1 | 9/2006 | Gardner, Jr. et al. |
| 2006/0254522 A1 | 11/2006 | Shaw |
| 2006/0256330 A1 | 11/2006 | Leipertz |
| 2006/0262304 A1 | 11/2006 | Carron |
| 2006/0268266 A1 | 11/2006 | Gardner |
| 2007/0007364 A1 | 1/2007 | Sliwa |
| 2007/0081156 A1 | 4/2007 | Treado |
| 2007/0086624 A1 | 4/2007 | Breed et al. |
| 2007/0098142 A1 | 5/2007 | Rothschild |
| 2007/0118324 A1 | 5/2007 | Gulati |
| 2007/0125951 A1 | 6/2007 | Snider |
| 2007/0127030 A1 | 6/2007 | Shpantzer |
| 2007/0153268 A1 | 7/2007 | Panza et al. |
| 2007/0163431 A1 | 7/2007 | Mohar |
| 2007/0216898 A1 | 9/2007 | Gardner |
| 2007/0262574 A1 | 11/2007 | Breed |
| 2007/0268485 A1 | 11/2007 | Polonskiy |
| 2007/0282506 A1 | 12/2007 | Breed et al. |
| 2008/0036580 A1 | 2/2008 | Breed |
| 2008/0036593 A1 | 2/2008 | Rose-Pehrsson |
| 2008/0051957 A1 | 2/2008 | Breed et al. |
| 2008/0084560 A1 | 4/2008 | Zhang |
| 2008/0088837 A1 | 4/2008 | Gardner |
| 2008/0129581 A1 | 6/2008 | Douglass |
| 2008/0144885 A1 | 6/2008 | Zucherman |
| 2008/0154535 A1 | 6/2008 | Sparks |
| 2008/0157940 A1 | 7/2008 | Breed |
| 2008/0165344 A1 | 7/2008 | Treado |
| 2008/0180675 A1 | 7/2008 | Sheen |
| 2008/0191137 A1 | 8/2008 | Poteet |
| 2008/0198365 A1 | 8/2008 | Treado |
| 2008/0204757 A1 | 8/2008 | Manning |
| 2008/0236275 A1 | 10/2008 | Breed |
| 2008/0258071 A1 | 10/2008 | Arnold |
| 2008/0268548 A1 | 10/2008 | Zuckerman |
| 2008/0295783 A1 | 12/2008 | Furton |
| 2009/0046538 A1 | 2/2009 | Breed |
| 2009/0092284 A1 | 4/2009 | Breed et al. |
| 2009/0095885 A1 | 4/2009 | Hager |
| 2009/0101843 A1 | 4/2009 | Henshaw |
| 2009/0128802 A1 | 5/2009 | Treado et al. |
| 2009/0202128 A1 | 8/2009 | Gorian et al. |
| 2009/0236528 A1 | 9/2009 | Shpantzer |
| 2009/0252650 A1 | 10/2009 | Lakshmanan |
| 2009/0257555 A1 | 10/2009 | Chalmers |

FOREIGN PATENT DOCUMENTS

| | | |
|---|---|---|
| WO | WO/01/33212 | 5/2001 |
| WO | WO/03/059735 | 7/2003 |
| WO | WO/03/102534 | 11/2003 |
| WO | WO/2005/008198 | 1/2005 |
| WO | WO/2005008200 | 1/2005 |
| WO | WO/2005/010474 | 3/2005 |
| WO | WO/2007/001379 | 1/2007 |
| WO | WO/2007/011391 | 1/2007 |
| WO | WO/2007/013000 | 2/2007 |
| WO | WO/2007/032814 | 3/2007 |
| WO | WO/2007/044067 | 4/2007 |
| WO | WO/2007/044593 | 4/2007 |
| WO | WO/2007/051092 | 5/2007 |
| WO | WO/2007/056753 | 5/2007 |
| WO | WO/2007/084099 | 7/2007 |
| WO | WO/2007/101297 | 9/2007 |
| WO | WO/2007/120996 | 10/2007 |
| WO | PCT/US06/22647 | 11/2007 |
| WO | WO/2007/103897 | 11/2007 |
| WO | WO/2007/123555 | 11/2007 |
| WO | WO/2008/002659 | 1/2008 |
| WO | WO/2008/010832 | 1/2008 |
| WO | WO/2008/048979 | 4/2008 |
| WO | WO/2008/024344 | 6/2008 |
| WO | WO/2008/097272 | 8/2008 |
| WO | WO/2008/105812 | 9/2008 |
| WO | WO/2008/140473 | 11/2008 |

OTHER PUBLICATIONS

Sharma, et al, Portable Stand-off Raman and Mie-Rayleigh LIDAR for Cloud, Aerosols, and Chemical Monitoring, Proceedings of SPIE vol. 5154, LIDAR Remote Sensing for Environmental Monitoring IV, pp. 1-14, 2003.

Sharma, et al., Remote Pulsed Laser Raman Spectroscopy System for Mineral Analysis on Planetary Surfaces to 66 Meters, Applied Spectroscopy. vol. 56, No. 6, 2002, pp. 699-705.

PCT/US06/22647, Notification of Transmittal of the International Search Report and the Written Opinion of the International Searching Authority, Mar. 31, 2008.

Gardner, C. et al., "Remote Chemical Biological and Explosive Agent Detection Using a Robot-Based Raman Detector", SPIE Defense + Security. Proc. SPIE 6962. 69620T (2008).

Pati, B. et al., "Passively Q-switched Nd:YLF laser in a D-rod configuration," in Conference on Lasers and Electro-Optics, OSA Technical Digest (Optical Society of America, Washington, DC 2008), paper CFJ5.

Fuller, M. et al., "High gain end pumped lasers," OSA TOPS; vol. 19, Advanced Solid State Lasers, Walter Bosenberg and Martin M. Feijer (eds), 1998, Optical Society of America.

Kyusho, Y et al., "High-energy subnanosecond compact laser system with diode-pumped, Q-switched Nd:YVO4laser," OSA TOPS on Advanced Solid State Lasers, vol. 1, Stephen A. Payne and Clifford Pollock (eds), 1996, Optical Society of America.

Zheng, S. et al., "Laser-diode end-pumped passively Q-switched laser with Cr4+:YAG saturable absorber," Opt. Engineering. vol. 41. # 9, 2002, pp. 2271-2275.

Nelson et al., "Single-Shot Multiwavelength Imaging of Laser Plumes." Applied Spectroscopy, vol. 52, No. 2, Feb. 1, 1998.

Extended European Search Report, PCT/US2006022647, Aug. 10, 2010.

* cited by examiner

```
┌─────────────────────────────────────────────────────────┐
│ illuminating a target area comprising at least one      │
│ unknown sample to thereby generate a plurality of first │
│ interacted photons wherein said first interacted        │
│ photons are selected from the group consisting of:      │ 110
│ photons absorbed by said target area, photons reflected │
│ by said target area, photons scattered by said target   │
│ area, photons emitted by said target area, and          │
│ combinations thereof                                    │
└─────────────────────────────────────────────────────────┘
                            │
                            ▼
┌─────────────────────────────────────────────────────────┐
│ assessing said plurality of first interacted photons    │
│ using a spectroscopic device wherein said assessing     │ 120
│ comprises obtaining a SWIR data set representative of   │
│ said target area                                        │
└─────────────────────────────────────────────────────────┘
                            │
                            ▼
┌─────────────────────────────────────────────────────────┐
│ analyzing said SWIR data set to thereby identify an     │ 130
│ area of interest in said target area                    │
└─────────────────────────────────────────────────────────┘
                            │
                            ▼
┌─────────────────────────────────────────────────────────┐
│ illuminating said area of interest using a laser light  │
│ source to thereby generate a plurality of second        │
│ interacted photons wherein said second interacted       │
│ photons are selected from the group consisting of:      │ 140
│ photons absorbed by said area of interest, photons      │
│ reflected by said area of interest, photons scattered   │
│ by said area of interest, photons emitted by said area  │
│ of interest, and combinations thereof                   │
└─────────────────────────────────────────────────────────┘
                            │
                            ▼
┌─────────────────────────────────────────────────────────┐
│ assessing said plurality of second interacted photons   │
│ using a spectroscopic device wherein said assessing     │ 150
│ comprises obtaining a Raman data set representative of  │
│ said area of interest                                   │
└─────────────────────────────────────────────────────────┘
                            │
                            ▼
┌─────────────────────────────────────────────────────────┐
│ analyzing said Raman data set to thereby identify said  │
│ area of interest as comprising at least one of: an      │
│ explosive material, a concealment material, a           │ 160
│ formulation additive of an explosive material, a binder │
│ of an explosive material, a non-explosive material, and │
│ combinations thereof                                    │
└─────────────────────────────────────────────────────────┘
```

Figure 1

|  | Standard Raman detection | STAR – fixed detector array | STAR – moving detector array |
|---|---|---|---|
| Laser spot size (cm) | 5 | 5 | 5 |
| Y dimension of FOV (m) | 1 | 1 | 1 |
| X dimension of FOV (m) | 10 | 10 | 10 |
| Standoff distance (m) | 3 | 3 | 3 |
| Average time of move telescope (s) | 1 | N/A | N/A |
| Average time to move laser beam (s) | N/A | 0.01 | 1.00 |
| Time to acquire and process FAST Raman spectra (s) | 1 | 1 | 1 |
| Number of high probability areas targeted by SWIR | N/A | 4 | 4 |
| Average area of threat location (cm$^2$) | N/A | 400 | 400 |
| Time to interrogate FOV (s) | 5,093 | 0.81 | 81.49 |
| Sensor v. target velocity (m/sec) | 0.0020 | 12.27 | 0.1227 |
| Sensor v. target velocity (mph) | 0.00439 | 27.45 | 0.27 |
| Area search rate (m2/sec) | 0.00196 | 12.27 | 0.12 |

| 710 | illuminating a target area comprising at least one unknown sample to thereby generate a plurality of first interacted photons wherein said first interacted photons are selected from the group consisting of: photons absorbed by said target area, photons reflected by said target area, photons scattered by said target area, photons emitted by said target area, and combinations thereof |

↓

720: assessing said first interacted photons to thereby generate a SWIR hyperspectral image representative of said target area

↓

730: analyzing said SWIR hyperspectral image representative of said target area to thereby identify an area of interest

↓

740: illuminating said area of interest to thereby generate a plurality of second interacted photons wherein said second interacted photons are selected from the group consisting of photons absorbed by said area of interest, photons reflected by said area of interest, photons scattered by said area of interest, photons emitted by said area of interest, and combinations thereof

↓

750: assessing said second interacted photons to thereby generate a plurality of spatially resolved Raman spectra representative of said area of interest

↓

760: analyzing said Raman spectra to thereby identify said area of interest as comprising at least one of: an explosive material, a concealment material, a formulation additive of an explosive material, a binder of an explosive material, a non-explosive material, and combinations thereof

Figure 7

- CONDOR-ST (G2) SWIR HSI detects and identifies explosive residues on slate substrates at 40m standoff range.
- Residues present in $mg/cm^2$ concentration.
- Ammonium nitrate (AN) concentration (est.) = $2\ mg/cm^2$
- AN LOD 70 $\mu g/cm^2$ @ 40m
- Increased optical magnification results in improvement of AN LOD to 0.9 $\mu g/cm^2$
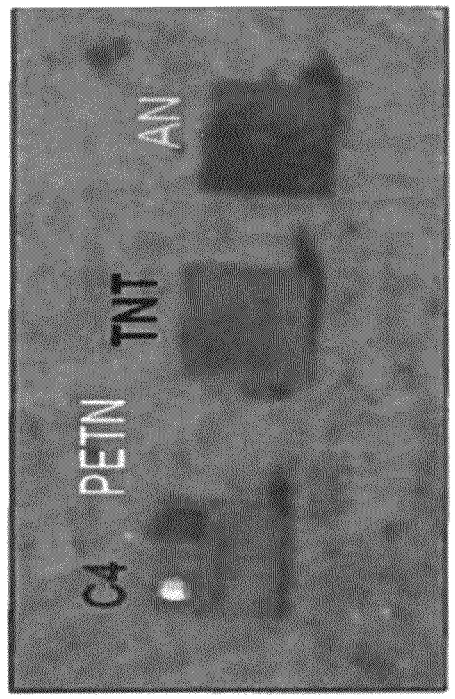
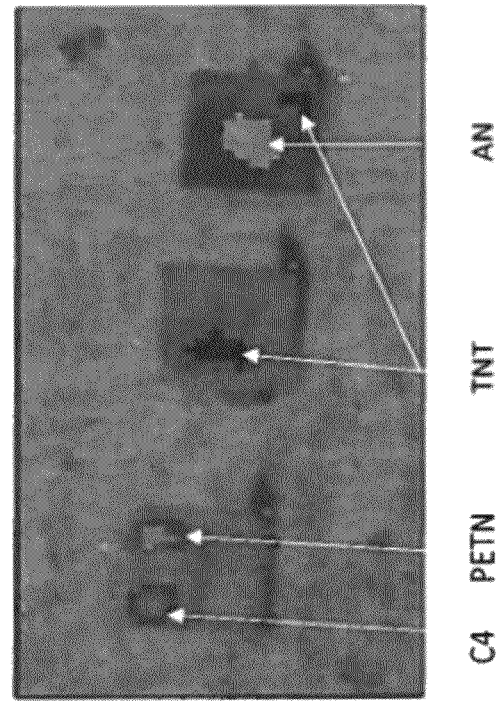
Figure 9

CONDOR-ST (SWIR HSI) on the move (OTM) real-time detection of ammonium nitrate (AN) residue deposited on the ground at standoff distance of >50m. Standoff data collected while moving at 3-5mph. Pixels containing AN are pseudo-colored red to indicate positive detection.

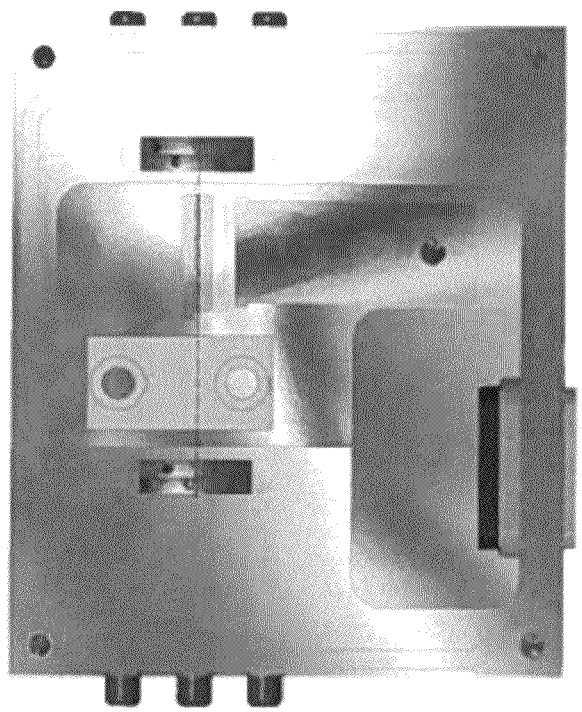
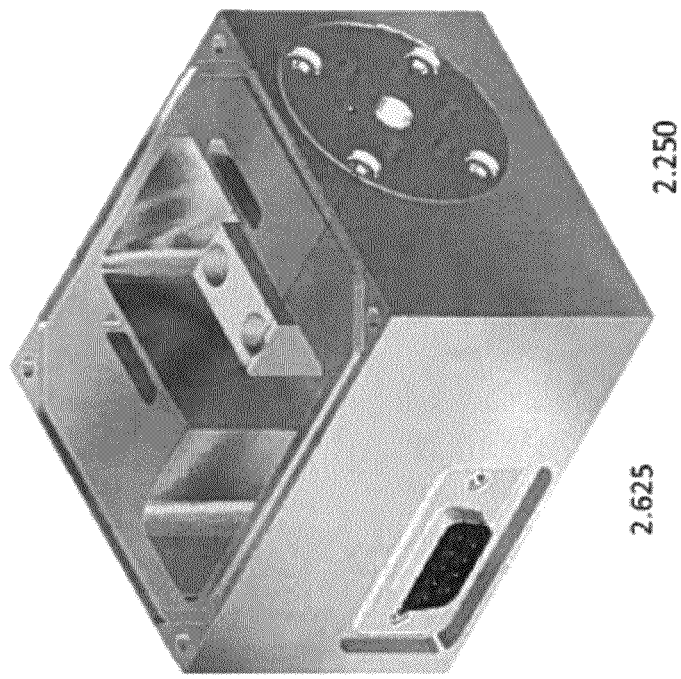
Figure 12

SWIR TARGETED AGILE RAMAN (STAR) SYSTEM FOR ON-THE-MOVE DETECTION OF EMPLACE EXPLOSIVES

RELATED APPLICATIONS

This Application is a continuation-in-part of U.S. patent application Ser. No. 12/199,145, filed on Aug. 27, 2008, now U.S. Pat. No. 8,054,454 entitled "Time and Space Resolved Standoff Hyperspectral IED Explosives LIDAR Detector" and U.S. patent application Ser. No. 12/754,229, filed on Apr. 5, 2010, entitled "Chemical Imaging Explosives (CHIMED) Optical Sensor Using SWIR."

This Application also claims priority under 35 U.S.C .scnt.119(e) to the following U.S. Provisional Patent Application: 61/268,885, filed on Jun. 17, 2009, entitled "SWIR Targeted Agile Raman (STAR) System for the OTM Detection of Emplace Explosives; 61/278,393, filed on Oct. 6, 2009, entitled "Use of Magnification to Increase SWIR HSI Detection Sensitivity"; 61/335,785, filed on Jan. 12, 2010, entitled "System and Method for SWIR HSI for Daytime and Nighttime Operations; 61/301,814, filed on Feb. 5, 2010, entitled "System and Method for Detection of Hazardous Agents Using SWIR, MWIR, and LWIR"; 61/395,440, filed on May 13, 2010, entitled "Portable System for Detecting Explosives and Method for Use Thereof"; 61/324,963, filed on Apr. 16, 2010, entitled "SWIR MCF"; and 61/305,667, filed on Feb. 18, 2010, entitled "System and Method for Detecting Explosives on Shoes and Clothing".

Each of the above referenced applications is hereby incorporated by reference in their entireties.

This invention was made with government support under N00174-10-C-0029 awarded by Naval Sea Systems Command (NAVSEA). The government has certain rights in the invention.

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise an illumination source, image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, telescopes are appropriate image gathering optics.

For detection of images formed by the various optical systems, two-dimensional, imaging focal plane array (FPA) detectors are typically employed. The choice of FPA detector is governed by the spectroscopic technique employed to characterize the sample of interest. For example, silicon (Si) charge-coupled device (CCD) detectors or CMOS detectors are typically employed with visible wavelength fluorescence and Raman spectroscopic imaging systems, while indium gallium arsenide (InGaAs) FPA detectors are typically employed with near-infrared spectroscopic imaging systems.

Spectroscopic imaging of a sample can be implemented by one of two methods. First, a point-source illumination can be provided on the sample to measure the spectra at each point of the illuminated area. Second, spectra can be collected over the an entire area encompassing the sample simultaneously using an electronically tunable optical imaging filter such as an acousto-optic tunable filter (AOTF) or a liquid crystal tunable filter ("LCTF"). Here, the organic material in such optical filters are actively aligned by applied voltages to produce the desired bandpass and transmission function. The spectra obtained for each pixel of such an image thereby forms a complex data set referred to as a hyperspectral image which contains the intensity values at numerous wavelengths or the wavelength dependence of each pixel element in this image.

Spectroscopic devices operate over a range of wavelengths due to the operation ranges of the detectors or tunable filters possible. This enables analysis in the Ultraviolet (UV), visible (VIS), near infrared (NIR), short-wave infrared (SWIR), mid infrared (MIR) wavelengths and to some overlapping ranges. These correspond to wavelengths of about 180-380 nm (UV), 380-700 nm (VIS), 700-2500 nm (NIR), 900-1700 nm (SWIR), and 2500-25000 nm (MIR).

There exists a need for accurate and reliable detection of explosives and other materials at standoff distances. Additionally, it would be advantageous if a standoff system and method could be configured to operate in an On-the-Move (OTM) mode. It would also be advantageous if a system and method could be configured for deployment on a small unmanned ground vehicle (UGV).

SUMMARY OF INVENTION

The present invention relates generally to a system and method for detecting explosives and other materials in a sample scene. More specifically, the present disclosure relates to a system and method for detecting explosives and other materials using SWIR hyperspectral imaging in a targeting mode to define an area of interest within a target area and Raman spectroscopy in an identification mode to determine whether the area of interest comprises an explosive material. One term that may be used to describe the system and method of the present disclosure is Agile Laser Scanning ("ALS") Raman spectroscopy. The term is used to describe the ability to focus the area of interrogation by Raman spectroscopy to those areas defined by SWIR hyperspectral imaging with high probabilities of comprising explosives.

SWIR hyperspectral imaging may be implemented to define areas where the probability of finding explosive threats is high. The advantage of using SWIR is its speed of analysis. Raman spectroscopy provides for chemical specificity and may therefore be implemented to interrogate those areas of interest identified by the SWIR hyperspectral image to determine the presence or absence of explosive material. The present disclosure provides for a system and method that combines these two techniques, using the strengths of each, to provide for a novel technique of achieving rapid, reliable, and accurate evaluation of unknown materials. The system and method also hold potential for providing autonomous operation as well as providing considerable flexibility for an operator to tailor searching for specific applications.

The present disclosure contemplates both static and On-the-Move ("OTM") standoff configurations. The present disclosure also contemplates the implementation of the sensor system of the present disclosure onto an Unmanned Ground Vehicle ("UGV"). Integration of these sensors onto small UGV platforms in conjunction with specific laser systems may be configured to achieve a pulsed laser system with a size, weight, and power consumption compatible with small UGV operation. Such a configuration holds potential for implementation in a laser-based OTM explosive location system on a small UGV.

The present disclosure also provides for the application of various algorithms to provide for data analysis and object imaging and tracking. These algorithms may further comprise image-based explosive detection algorithms, including tools that may determine the size, in addition to identity and location, of explosive materials. Providing this information to an operator in a defeat/destroy system may hold potential for determining the magnitude of explosive threats in a wide area surveillance mode. Additionally, algorithms may be applied to provide for sensor fusion. This fusion of SWIR and Raman data holds potential for reducing false alarm rates.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

The patent or application file contains at least one drawing executed in color. Copies of this patent or patent application publication with color drawing(s) will be provided by the Office upon request and payment of the necessary fee.

FIG. 1 is illustrative of a method of the present disclosure.

FIG. 2 is a comparison between standard Raman detection and the detection system and method of the present disclosure.

FIG. 7 is illustrative of a method of the present disclosure.

FIG. 9 represents the detection capabilities of the system and method of the present disclosure.

FIG. 12 is a schematic representation of an exemplary packaging option of the system of the present disclosure.

DETAILED DESCRIPTION

Figure 3:
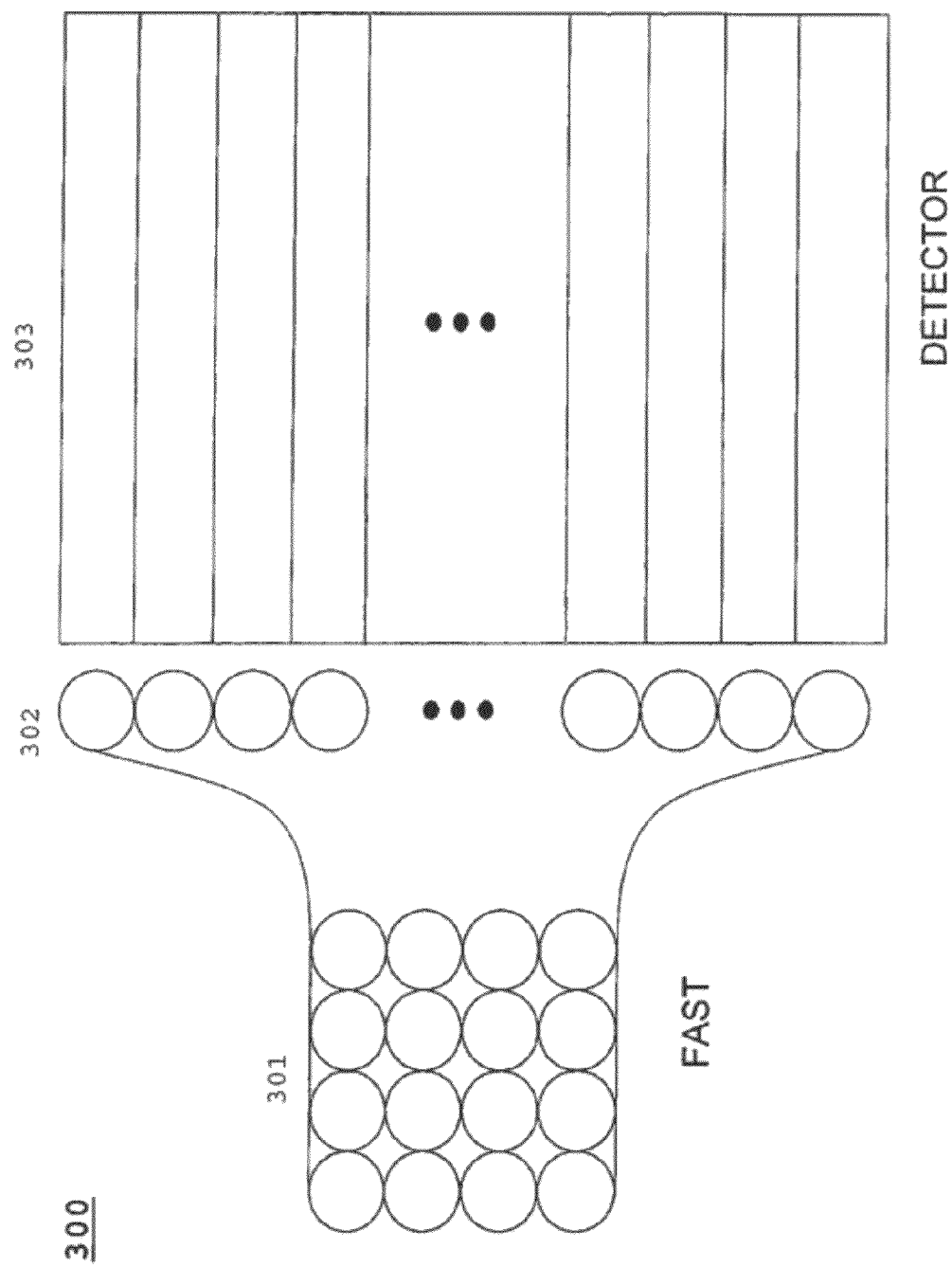
FIG. 3 is a schematic representation of a FAST device.

Reference will now be made in detail to the embodiments of the present disclosure, examples of which are illustrated in the accompanying drawings. Wherever possible, the same reference numbers will be used throughout the drawings to refer to the same or like parts.

The present disclosure provides for a system and method for detecting explosives and other materials at standoff distances using SWIR and Raman spectroscopic methods. FIG. 1 is illustrative of one embodiment of a method of the present disclosure. The method 100 provides for illuminating a target area in step 110 to thereby generate a plurality of first interacted photons. These first interacted photons may be selected from the group consisting of: photons absorbed by said target area, photons reflected by said target area, photons scattered by said target area, photons emitted by said target area, and combinations thereof. In one embodiment of the present disclosure, the target area is illuminated using a solar radiation source (i.e., the sun). In one embodiment, the target area may be selected as a result of surveying a sample scene. Such knowledge of the sample area and/or field of view ("FOV") may be valuable for operator control and for sensor fusion. This may be accomplished using a video capture device which outputs a dynamic image of the sample scene. In one embodiment, the video capture device may comprise a color video camera. The dynamic image may then be analyzed and a target area selected based on at least one of: size, shape, color, or other attribute of one or more objects in the sample scene. These objects may comprise unknown samples which are suspected of comprising explosive materials.

The plurality of first interacted photons is assessed in step 120 using a spectroscopic device wherein said assessing comprises obtaining a test SWIR data set representative of a target area. In one embodiment the test SWIR data set may comprise at least one of: a plurality of spatially resolved SWIR spectra representative of the target area and a SWIR image representative of the target area. The SWIR image may comprise a hyperspectral image. The SWIR image may also comprise a multispectral image or other chemical image. A hyperspectral image comprises an image and a fully resolved spectrum unique to the material for each pixel location in said image. In one embodiment, the SWIR image may comprise a spatially-accurate wavelength resolved image.

In step 130 the test SWIR data set is analyzed to thereby identify an area of interest within said target area. This area of interest may be selected based on the likelihood an explosive material is present in that location.

In one embodiment, analyzing the test SWIR data set may comprise comparing the test SWIR data set to a plurality of reference SWIR data sets in a reference database. These reference SWIR data sets may each be associated with a known material. If the comparison between the test SWIR data set and a reference SWIR data set, then the unknown material present in the area of interest may be identified as the known material.

The area of interest is illuminated in step 140 to thereby generate a plurality of second interacted photons. These second interacted photons may be selected from the group consisting of: photons absorbed by said area of interest, photons reflected by said area of interest, photons scattered by said area of interest, photons emitted by said area of interest, and combinations thereof. In one embodiment, the area of interest is illuminated using a laser light source.

In one embodiment, the method of the present disclosure may provide for illuminating the area of interest using pulsed laser excitation and collecting said second plurality of interacted photons using time-gated detection. In one embodiment, a nanosecond laser pulse is applied to the area of interest. Additionally, a detector whose acquisition "window" can be precisely synchronized to this pulse is used. Use of pulsed laser illumination and time-gated detection for detecting threat agents is more fully described in U.S. patent application Ser. No. 12/619,336, filed on Nov. 16, 2009, entitled "Raman Chemical Imaging of Threat Agents Using Pulsed Laser Excitation and Time-Gated Detection", which is hereby incorporated by reference in its entirety.

The second plurality of interacted photons are assessed in step 150 using a spectroscopic device wherein said assessing comprises obtaining a test Raman data set representative of said area of interest. In one embodiment, said test Raman data set may comprise at least one of: a plurality of spatially resolved Raman spectra representative of said area of interest and a Raman image representative of said area of interest.

In step 160 said test Raman data set is analyzed to thereby identify said area of interest as comprising at least one of: an explosive material, a concealment material, a formulation additive of an explosive material, a formulation additive of an explosive material, a binder of an explosive material, a non-explosive material, and combinations thereof.

In one embodiment, analyzing the test Raman data set may comprise comparing the test Raman data set to a plurality of reference Raman data sets in a reference database. These reference Raman data sets may each be associated with a known material. If the comparison between the test Raman data set and a reference Raman data set, then the unknown material present in the area of interest may be identified as the known material.

Comparisons between a test SWIR data set and a test Raman data set to reference data sets may be accomplished using one or more chemometric techniques and/or pattern recognition algorithms. The applied technique may be selected from the group consisting of: principle components analysis, partial least squares discriminate analysis, cosine correlation analysis, Euclidian distance analysis, k-means clustering, multivariate curve resolution, band t. entropy method, mahalanobis distance, adaptive subspace detector, spectral mixture resolution, Bayesian fusion, and combinations thereof.

In one embodiment, the method may further comprise passing at least one of said first plurality of interacted photons and said second plurality of interacted photons through a filter. In one embodiment, the filter may be a filter selected from the group consisting of: a multi-conjugate tunable filter, a liquid crystal tunable filter, acousto-optical tunable filters, Lyot liquid crystal tunable filter, Evans Split-Element liquid crystal tunable filter, Solc liquid crystal tunable filter, Ferroelectric liquid crystal tunable filter, Fabry Perot liquid crystal tunable filter, and combinations thereof.

In one embodiment, the filter may comprise multi-conjugate filter technology available from ChemImage Corporation, Pittsburgh, Pa. This technology is more fully described in U.S. Pat. No. 7,362,489, filed on Apr. 22, 2005, entitled "Multi-Conjugate Liquid Crystal Tunable Filter" and U.S. Pat. No. 6,692,809, filed on Feb. 2, 2005, also entitled "Multi-Conjugate Liquid Crystal Tunable Filter." In another embodiment, the MCF technology used may comprise a SWIR multi-conjugate tunable filter. One such filter is described in U.S. Patent Application No. 61/324,963, filed on Apr. 16, 2010, entitled "SWIR MCF". Each of these patents are hereby incorporated by reference in their entireties.

In one embodiment, the method may comprise passing said second plurality of interacted photons through a fiber array spectral translator ("FAST") device. A FAST device, when used in conjunction with a photon detector, allows massively parallel acquisition of full-spectral images. A FAST device can provide rapid real-time analysis for quick detection, classification, identification, and visualization of the sample. The FAST technology can acquire a few to thousands of full spectral range, spatially resolved spectra simultaneously. A typical FAST array contains multiple optical fibers that may be arranged in a two-dimensional array on one end and a one dimensional (i.e., linear) array on the other end. The linear array is useful for interfacing with a photon detector, such as a charge-coupled device ("CCD"). The two-dimensional array end of the FAST is typically positioned to receive photons from a sample. The photons from the sample may be, for example, emitted by the sample, absorbed by the sample, reflected off of the sample, refracted by the sample, fluoresce from the sample, or scattered by the sample. The scattered photons may be Raman photons.

In a FAST spectrographic system, photons incident to the two-dimensional end of the FAST may be focused so that a spectroscopic image of the sample is conveyed onto the two-dimensional array of optical fibers. The two-dimensional array of optical fibers may be drawn into a one-dimensional distal array with, for example, serpentine ordering. The one-dimensional fiber stack may be operatively coupled to an imaging spectrometer of a photon detector, such as a charge-coupled device so as to apply the photons received at the two-dimensional end of the FAST to the detector rows of the photon detector.

One advantage of this type of apparatus over other spectroscopic apparatus is speed of analysis. A complete spectroscopic imaging data set can be acquired in the amount of time it takes to generate a single spectrum from a given material. Additionally, the FAST can be implemented with multiple detectors. A FAST system may be used in a variety of situations to help resolve difficult spectrographic problems such as the presence of polymorphs of a compound, sometimes referred to as spectral unmixing.

FAST technology can be applied to the collection of spatially resolved Raman spectra. In a standard Raman spectroscopic sensor, a laser beam is directed on to a sample area, an appropriate lens is used to collect the Raman scattered light, the light is passed through a filter to remove light scattered at the laser wavelength and finally sent to the input of a spectrometer where the light is separated into its component wavelengths dispersed at the focal plane of a CCD camera for detection. In the FAST approach, the Raman scattered light, after removal of the laser light, is focused onto the input of a fiber optic bundle consisting of up to hundreds of individual fiber, each fiber collecting the light scattered by a specific location in the excited area of the sample. The output end of each of the individual fibers is aligned at the input slit of a spectrometer that is designed to give a separate dispersive spectrum from each fiber. A 2-dimensional CCD detector is used to capture each of these FAST spectra. As a result, multiple Raman spectra and therefore, multiple interrogations of the sample area can be obtained in a single measurement cycle, in essentially the same time as in conventional Raman sensors.

In one embodiment, an area of interest can be optically matched by the FAST array to the area of the laser spot to maximize the collection Raman efficiency. In one embodiment, the present disclosure contemplates another configuration in which only the laser beam be moved for scanning within a FOV. It is possible to optically match the SWIR FOV with the Raman collection FOV. The FOV is imaged onto a rectangular FAST array so that each FAST fiber is collecting light from one region of the FOV. The area per fiber which yields the maximum spatial resolution is easily calculated by dividing the area of the entire FOV by the number of fibers. Raman scattering is only generated when the laser excites a sample, so Raman spectra will only be obtained at those fibers whose collection area is being scanned by the laser beam. Scanning only the laser beam is a rapid process that may utilize by off-the-shelf galvanometer-driven mirror systems. An estimate of the speed advantage of this approach versus conventional detection systems is presented FIG. 2 which estimates of the increase in area scanning speed.

The construction of the FAST array requires knowledge of the position of each fiber at both the imaging end and the distal end of the array as shown, for example, in the diagram of FIG. 3 where a total of sixteen fibers are shown numbered in correspondence between the imaging end 301 and the distal end 302 of the fiber bundle. As shown in FIG. 3, a FAST fiber bundle 300 may feed optical information from its two-dimensional non-linear imaging end 301 (which can be in any non-linear configuration, e.g., circular, square, rectangular, etc.) to its one-dimensional linear distal end 302, which feeds the optical information into associated detector rows 303. The distal end may be positioned at the input to a photon detector 303, such as a CCD, a complementary metal oxide semiconductor ("CMOS") detector, or a focal plane array sensor (such as InGaAs, InSb, metal oxide semiconductor controlled thyristor ("MCT"), etc.). Photons exiting the distal end fibers may be collected by the various detector rows. Each fiber collects light from a fixed position in the two-dimensional array (imaging end) and transmits this light onto a fixed position on the detector (through that fiber's distal end).

Figure 4:
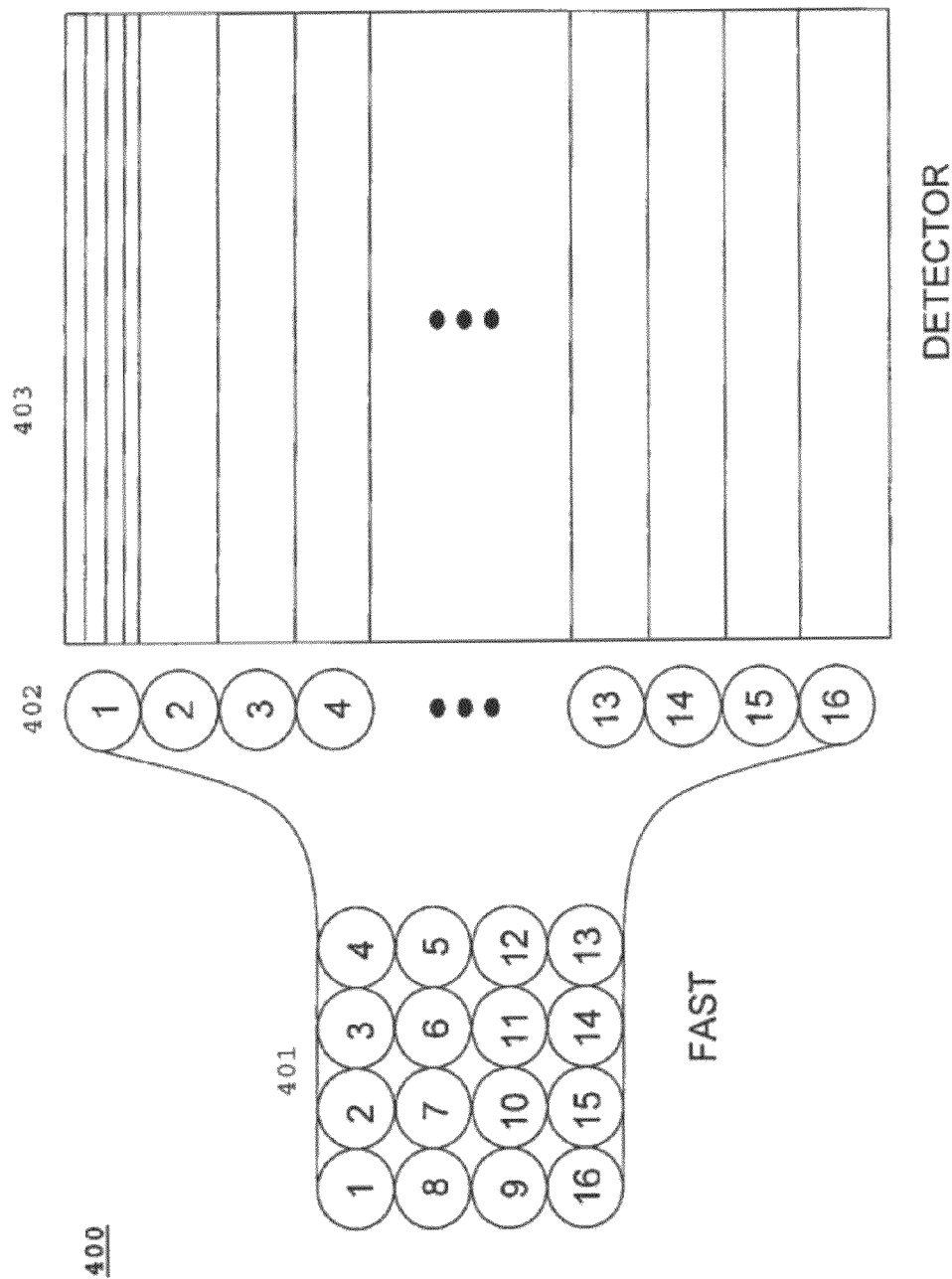
FIG. 4 is a schematic representation of a FAST device illustrating spatial knowledge of the various fibers.

FIG. 4 is a schematic representation of a non-limiting exemplary spatial arrangement of fibers at the imaging end 401 and the distal end 402. Additionally, as shown in FIG. 4, each fiber of the FAST fiber bundle 400 may span more than one detector row in detector 403, allowing higher resolution than one pixel per fiber in the reconstructed image. A system and method for spectral calibration of a spectroscopic system which includes a fiber array spectral translator is more fully described in U.S. Pat. No. 7,474,395, filed on Feb. 13, 2007 entitled, "System and Method for Image Reconstruction in a Fiber Array Spectral Translator System," which is hereby incorporated by reference in its entirety.

Figure 5:
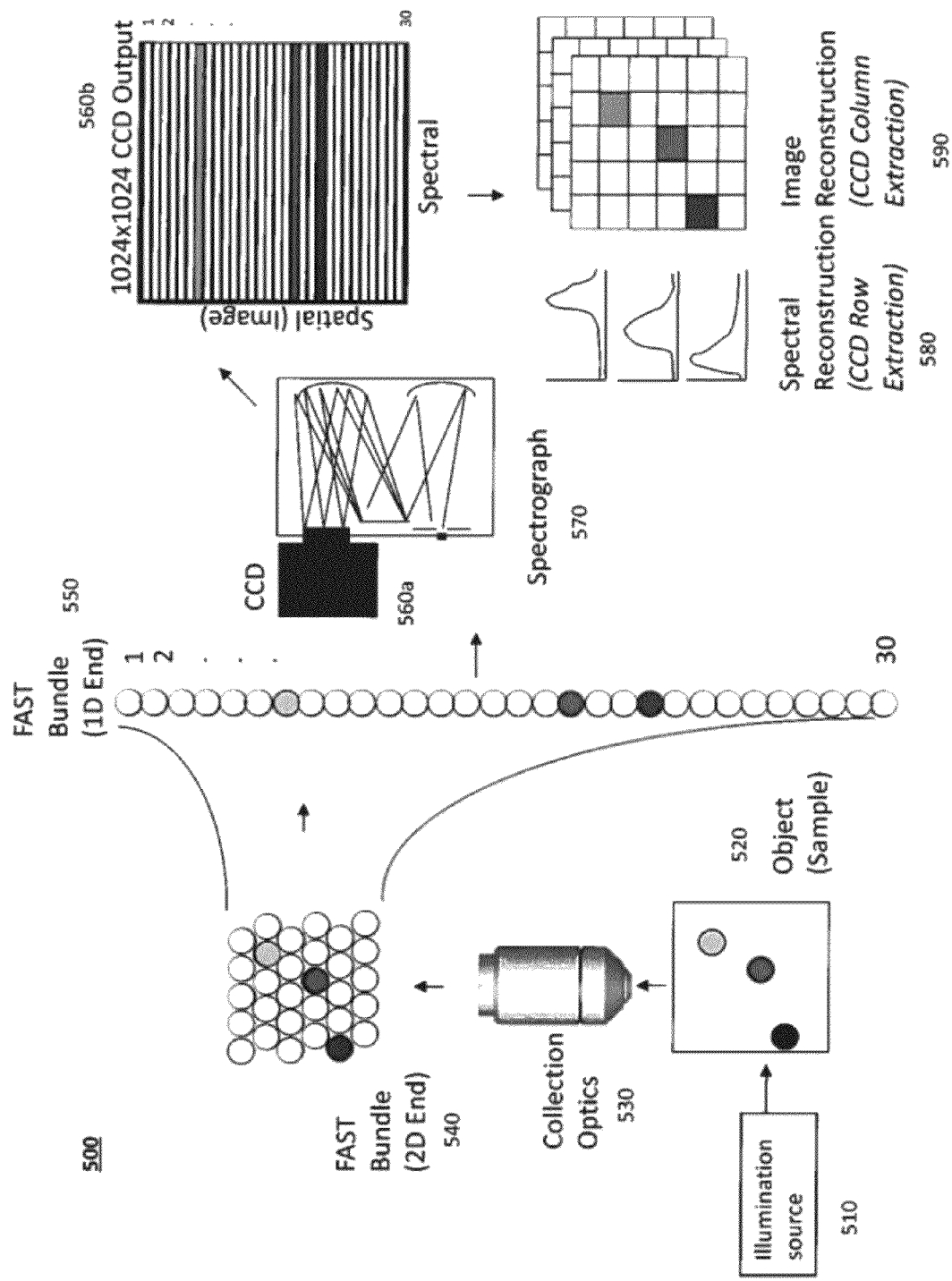
FIG. 5 is illustrative of the FAST device and its basic operation.

FIG. 5 is a schematic representation of a system comprising a traditional FAST device. The knowledge of the position of each fiber at both the imaging end and the distal end of the array and each associated spectra is illustrated in FIG. 5 by labeling these fibers, or groups of fibers) A, B, and C, and my assigning each a color.

The system 500 comprises an illumination source 510 to illuminate a sample 520 to thereby generate interacted photons. These interacted photons may comprise photons selected from the group consisting of: photons scattered by the sample, photons absorbed by the sample, photons reflected by the sample, photons emitted by the sample, and combinations thereof. These photons are then collected by collection optics 530 and received by a two-dimensional end of a FAST device 540 wherein said two-dimensional end comprises a two-dimensional array of optical fibers. The two-dimensional array of optical fibers is drawn into a one-dimensional fiber stack 550. The one-dimensional fiber stack is oriented at the entrance slit of a spectrograph 570. As can be seen from the schematic, the one-dimensional end 550 of a traditional FAST device comprises only one column of fibers. The spectrograph 570 may function to separate the plurality of photons into a plurality of wavelengths. The photons may be detected at a detector 560a to thereby obtain a spectroscopic data set representative of said sample. 560b is illustrative of the detector output, 580 is illustrative of spectral reconstruction, and 590 is illustrative of image reconstruction.

In another embodiment, the FAST device may be configured to provide for spatially and spectrally parallelized system. Such embodiment is more fully described in U.S. patent Ser. No. 12/759,082, filed on Apr. 13, 2010, entitled "Spatially and Spectrally Parallelized Fiber Array Spectral Translator System and Method of Use", which is hereby incorporated by reference in its entirety. Such techniques hold potential for enabling expansion of the number of fibers, which may improve image fidelity, and/or scanning area.

In addition to the systems and methods contemplated by the present disclosure, software may hold potential for collecting, processing and displaying chemical images from Raman data, similar to those generated in the SWIR HSI sensor. Such software may comprise ChemImage Xpert™ available from ChemImage Corporation, Pittsburgh, Pa.

In one embodiment, the method may further provide for applying a fusion algorithm to at least one of said Raman data set, said SWIR data set, and combinations thereof. In one embodiment, a chemometric technique may be applied to a data set wherein the data set comprises a multiple frame image. This results in a single frame image wherein each pixel has an associated score (referred to as a "scored image"). This score may comprise a probability value indicative of the probability the material at the given pixel comprises a specific material (i.e., an explosive material). In the present embodiment, a scored image may be obtained for both SWIR and Raman spectroscopic modalities. Bayesian fusion, multiplication, or another technique may be applied to these sets of scores to generate a fused score value. This fusion holds potential for increasing confidence in a result and reducing the rate of false positives. In one embodiment, this fused score value may be compared to a predetermined threshold or range of thresholds to generate a result. In another embodiment, weighting factors may be applied so that more reliable modalities are given more weight than less reliable modalities. Methods for sensor fusion are more fully described in U.S. patent application Ser. No. 11/450,138, filed on Jun. 9, 2006, entitled "Forensic Integrated Search Technology", U.S. patent application Ser. No. 12/017,445, filed on Jan. 22, 2008, entitled "Forensic Integrated Search Technology with Instrument Weight Factor Determination", and U.S. patent application Ser. No. 12/196,921, filed on Aug. 22, 2008, entitled "Adaptive Method for Outlier Detection and Spectral Library Augmentation." These applications are hereby incorporated by reference in their entireties.

In one embodiment, the method may further provide for "registration" of SWIR and Raman images. Such registration addresses the different image resolutions of different spectroscopic modalities which may result in differing pixel scales between the images of different modalities. Therefore, if the spatial resolution in the SWIR image is not equal to the spatial resolution in the Raman image, the portion of the SWIR image corresponding to the dimensions of the Raman image may be extracted out. This portion of the SWIR image may then be multiplied by the Raman image.

Figure 6:
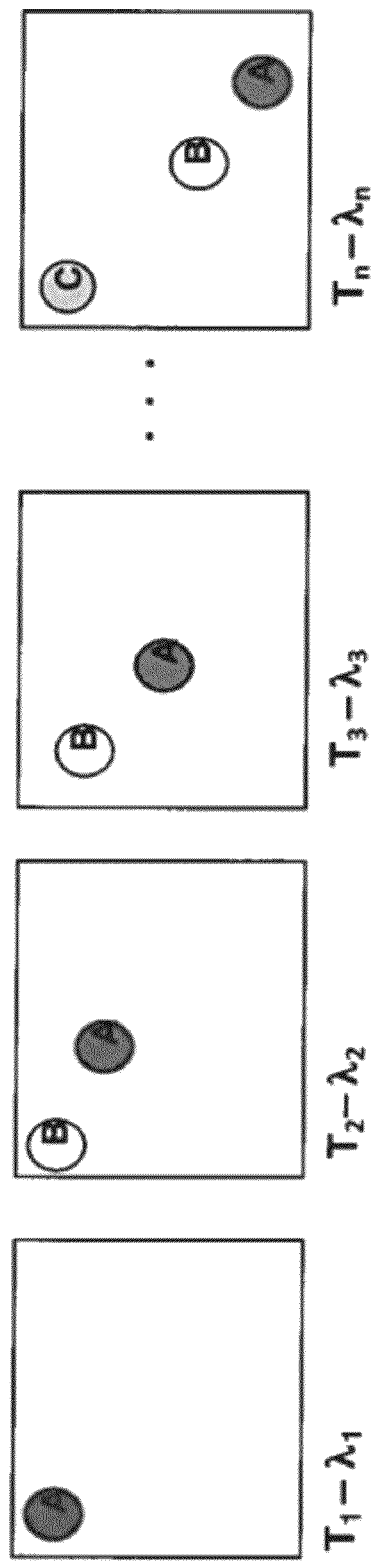
FIG. 6 is illustrative of a target-tracking algorithm of the present disclosure.

In one embodiment, the method may further comprise application of algorithms for at least one of: sensor fusion, data analysis, and target-tracking. One embodiment of a target tracking algorithm is illustrated in FIG. 6. The schematic illustrates a technique that may be implemented for dynamical chemical imaging in which more than one object of interest passes continuously through the FOV. Such continuous stream of objects results in the average amount of time required to collect all frames for a given object being equivalent to the amount of time required to capture one frame as the total number of frames under collection approaches infinity (frame collection rate reaches a steady state). In other words, the system is continually collecting the frames of data for multiple objects simultaneously and with every new frame, the set of frames for any single object is completed. In one embodiment, the objects of interest are of a size substantially smaller than the FOV to allow more than one object to be in the FOV at any given time.

Referring again to FIG. 6 Object A is present in a slightly translated position in every frame. Each frame is collected at a different wavelength. Tracking of Object A across all frames allows the spectrum to be generated for every pixel in Object A. The same process is followed for Object B and Object C.

A continual stream of objects can be imaged with the wavelengths being captured for every time, $t_i$, is updated in a continuous loop.

One method for dynamic chemical imaging is more fully described in U.S. Pat. No. 7,046,359, filed on Jun. 30, 2004, entitled "System and Method for Dynamic Chemical Imaging", which is hereby incorporated by reference in its entirety.

Another embodiment of a method of the present disclosure is illustrated in FIG. 7. The method 700 provides for illuminating a target area comprising at least one unknown sample in step 710 to thereby generate a plurality of first interacted photons wherein said first interacted photons are selected from the group consisting of: photons absorbed by said target area, photons reflected by said target area, photons scattered by said target area, photons emitted by said target area, and combinations thereof. In step 720 the first interacted photons are assessed to thereby generate a SWIR hyperspectral image representative of said target area. The SWIR hyperspectral image is analyzed in step 730 to thereby identify an area of interest. In step 740 the area of interest is illuminated to generate a plurality of second interacted photons wherein said second interacted photons are selected from the group consisting of: photons absorbed by said area of interest, photons reflected by said area of interest, photons scattered by said area of interest, photons emitted by said area of interest, and combinations thereof. Said second interacted photons are assessed in step 750 to thereby generate a plurality of spatially resolved Raman spectra representative of the area of interest.

In step 760 said Raman spectra are analyzed to thereby identify an area of interest as comprising at least one of: an explosive material, a concealment material, a formulation additive of an explosive material, a binder of an explosive material, a non-explosive material, and combinations thereof.

Figure 8:
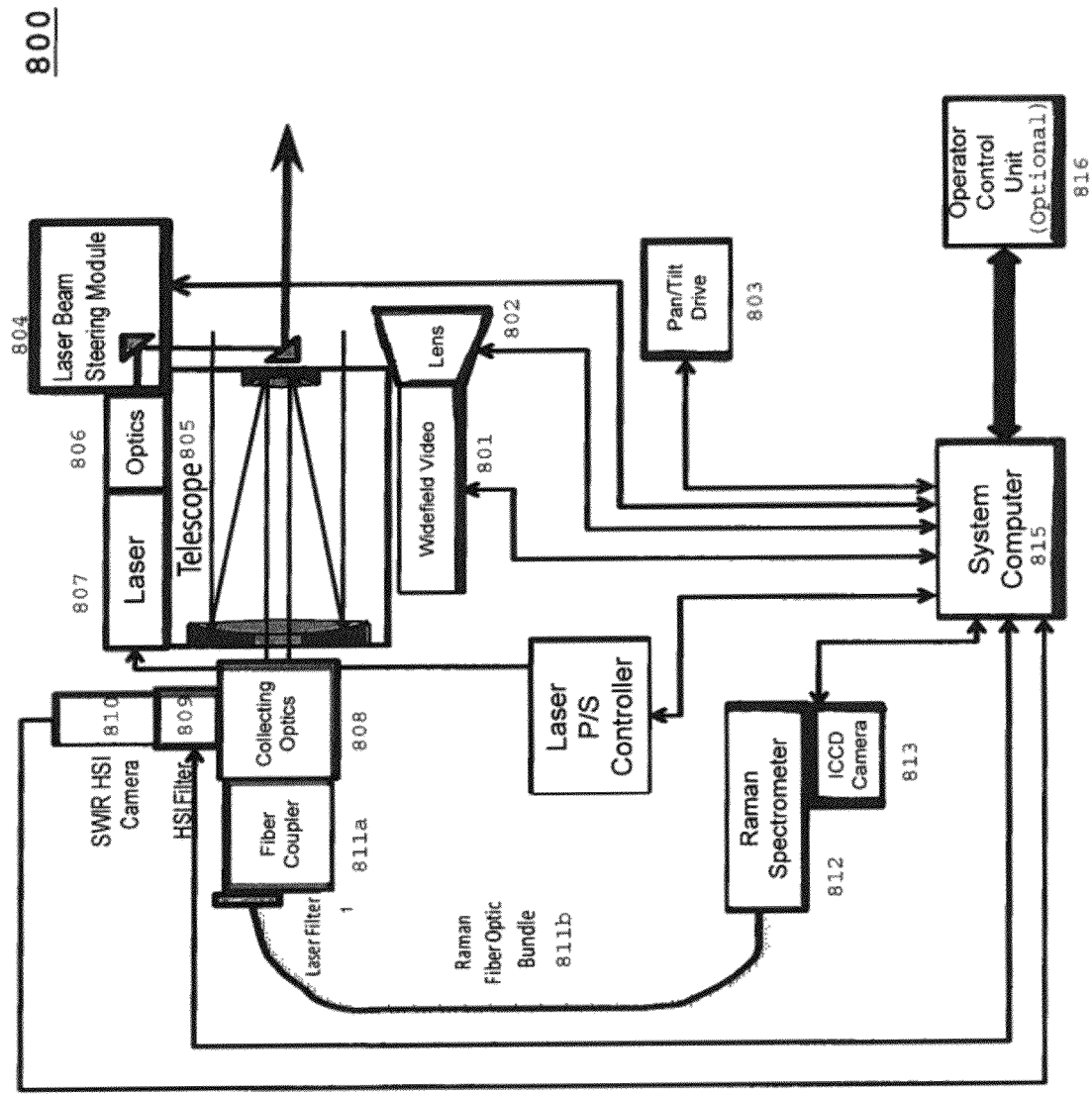
FIG. 8 is a schematic representation of a system of the present disclosure.

The present disclosure also provides for a system for detecting explosives and other materials. One embodiment of a system of the present disclosure is illustrated in FIG. 8. The system 800 comprises a first optical system coupled to a laser light source 807 for directing light to an area of interest in a target area. The optical system may further comprise optics 806, and laser beam steering module 804. In one embodiment, the laser light source 807 may comprise a Nd:YLF laser. The embodiment in FIG. 8 comprises the use of a telescope 805 to located and focus on at least one of a sample scene, a target area, an area of interest, and combinations thereof. However, the present disclosure is not limited to the use of a telescope and contemplates the use of any lens or lens system known in the art.

The system 800 may further comprise a second optical system. This second optical system may comprise a telescope 805 for collecting a first plurality of interacted photons and a second plurality of interacted photons, a coupling optic 808 which may further comprise a beamsplitter, to direct said first plurality of interacted photons to a first two-dimensional array of detection elements 810 and direct said second plurality of interacted photons to a FAST device comprising a fiber coupler 811a and a FAST device 811b.

The system 800 may further comprise a spectrometer 812 wherein the entrance slit of the spectrometer is coupled to said FAST device 811b to thereby generate a plurality of spatially resolved Raman spectra. A second two-dimensional array of detection elements 813 may be coupled to said spectrometer 812 and detect said spatially resolved Raman spectra to thereby generate at least one of: a plurality of spatially resolved Raman spectra and a Raman image.

The system may further comprise a filter 809 for sequentially filtering at least one of said first plurality of interacted photons and said second plurality of interacted photons in each of a plurality of predetermined wavelength bands.

The system may further comprise a video capture device 801 with an associated lens 802 wherein said video capture device outputs a dynamic image of at least one of: a sample scene, a target area, an area of interest, and combinations thereof.

The system may also comprise a pan/tilt unit 803 for controlling the position of the system, a laser P/S controller 814 for controlling the laser, and a system computer 815 for controlling the elements of the system. The system may also comprise an operator control unit 816 although this is not necessary. The operator control unit 816 may comprise the user controls for the system and may be a terminal, a lap top, a keyboard, a display screen, and the like.

In one embodiment, the system of the present disclosure is configured to operate in a pulsed laser excitation/time-gated detection configuration. This may be enabled by utilizing an ICCD detector. However, the present disclosure also contemplates the system may be configured in a continuous mode using at least one of: a continuous laser, a shutter, and a continuous camera.

Figure 10:
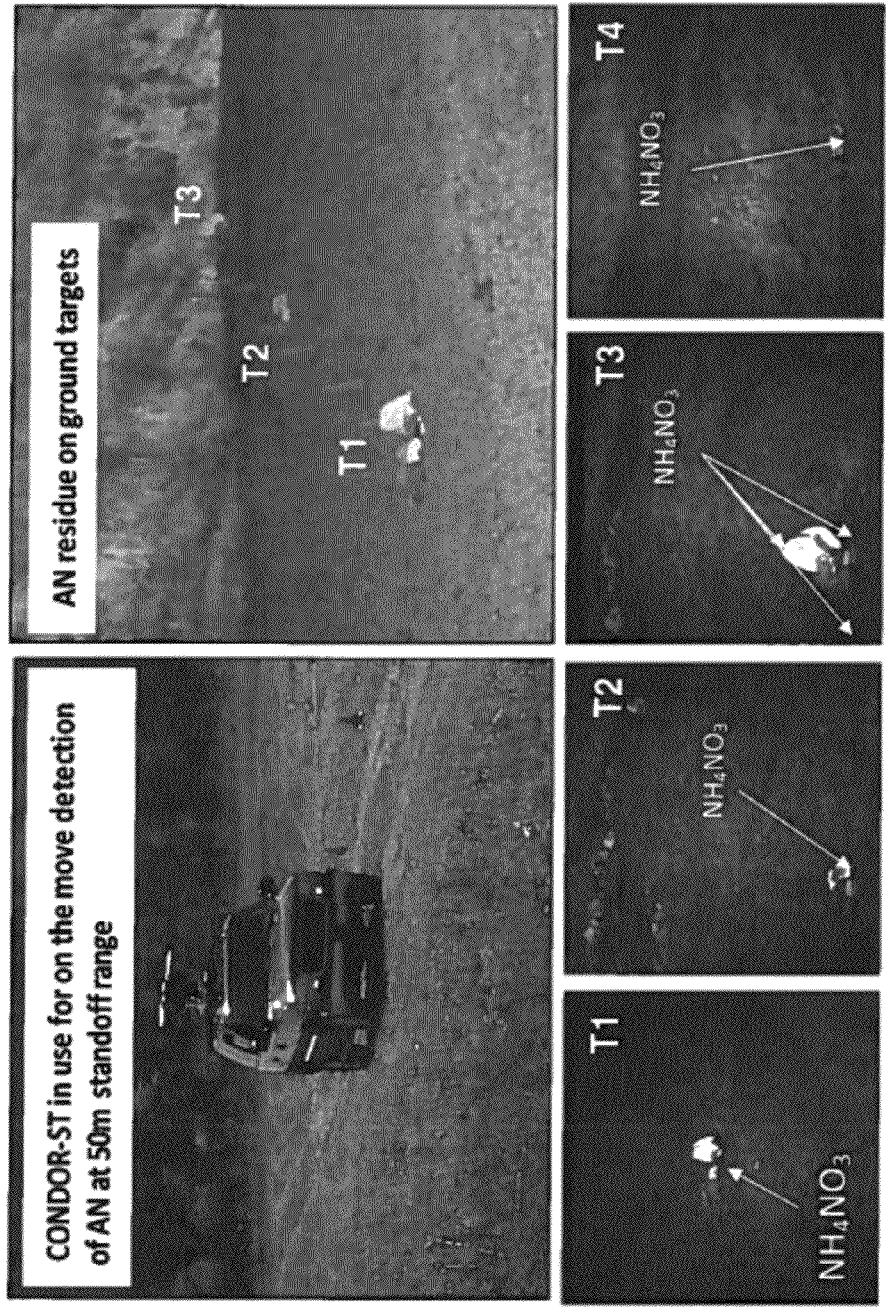
FIG. 10 represents the detection capabilities of the system and method of the present disclosure in an OTM configuration.

In one embodiment of the present disclosure, the SWIR portion of the system may comprise an InGaAs focal plane camera coupled to a wavelength-agile tunable filter and an appropriate focusing lens. Components may be selected to allow images generated by light reflecting off a target are to be collected over the 900 to 1700 nm wavelength region. This spectral region may be chosen because most explosives of interest exhibit molecular absorption in this region. Additionally, solar radiation (i.e., the sun) or a halogen lamp may be used as the light source in a reflected light measurement. The system may be configured to stare at a FOV or target area determined by the characteristics of the lens, and the tunable filter may be used to allow light at a single wavelength to reach the camera. By changing the wavelength of the tunable filter, the camera can take multiple images of the light reflected from a target area at wavelengths characteristic of various explosives and of background. These images can be rapidly processed to create chemical images, including hyperspectral images. In such images, the contrast is due to the presence or absence of a particular chemical or explosive material. The strength of SWIR hyperspectral imaging for OTM is that it is fast. Chemical images can be acquired, processed, and displayed quickly, in some instances in the order of tens of milliseconds. FIG. 9 shows typical static SWIR hyperspectral performance. The sensor detects and identifies explosive residues on slate substrates at 40m standoff range. FIG. 10 shows an example of OTM performance of a SWIR hyperspectral system. Ammonium nitrate ("AN") was detected at a standoff distance of >50 m while moving at a speed of 3-5 mph. Pixels in red indicate a positive AN detection.

The present disclosure also contemplates an embodiment wherein a sensing head is attached to a vehicle and operated via unbilical while the UGV is moved (full interrogation of the SWIR hyperspectral system on a UGV). In another embodiment, the sensor system described herein may be configured to operate via robotics. A small number of mounting brackets and plates may be fabricated in order to carry out the mounting sensor on the UGV.

Figure 11:
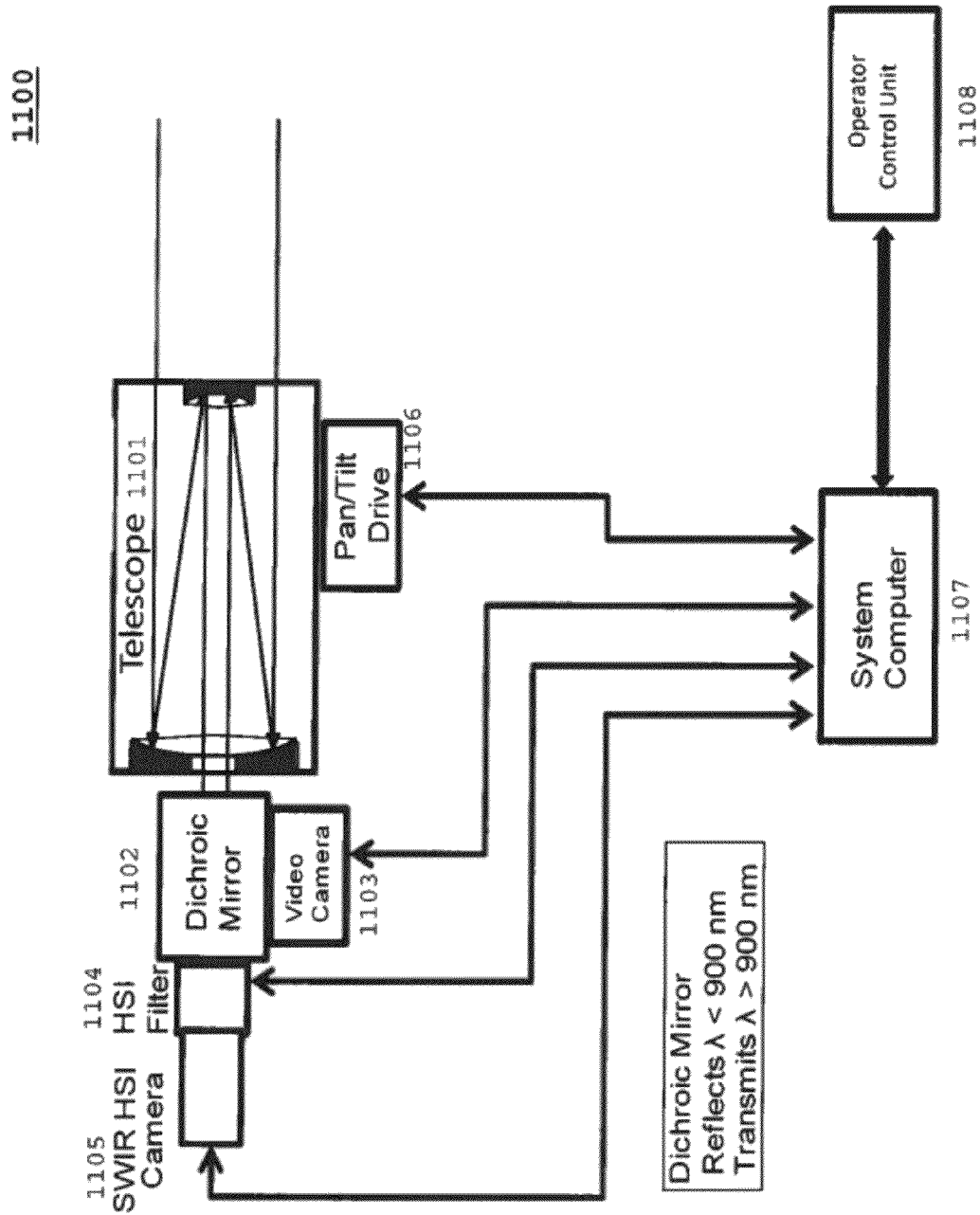
FIG. 11 is a schematic representation of a system of the present disclosure.

FIG. 11 is a schematic representation of another embodiment of the present disclosure. The system 1100 provides for a telescope 1101, for collecting interacted photons from a sample scene, a target area, an area of interest, and combinations thereof. A dichroic mirror 1102 and a filter 1104 is provided. The filter is provided to sequentially filter interacted photons in each of a plurality of predetermined wavelength bands. A two-dimensional array of detection elements 1105 is illustrated in FIG. 11 as comprising a SWIR HSI camera. The system may also comprise a video capture device, such as a video camera, 1103 that outputs a dynamic image of at least one of: a sample scene, a target area, an area of interest, and combinations thereof. The system may also comprise a pan/tilt unit 1106 to control the position of the system and a system computer 1107 to control the elements of the system. The system may also comprise an operator control unit 1108. If the imaging optic is of a reflective design (i.e., mirrors) versus a refractive design (i.e., lens) both the video camera and the SWIR camera can share this element. While reducing the system size and weight, this offers the advantage that both cameras are seeing the same FOV.

FIG. 12 is illustrative of exemplary packaging of one embodiment of the present disclosure. The figure illustrates solid models of a compact laser head design. In one embodiment, the laser may be 2.6×2.2×1.7 inches in size. In one embodiment, the present disclosure may implement CONDOR-ST technology, available from ChemImage Corporation, Pittsburgh, Pa. This technology maybe referred to commercially as "STAR", the "STAR System", and/or the "STAR Sensor".

Figure 13:
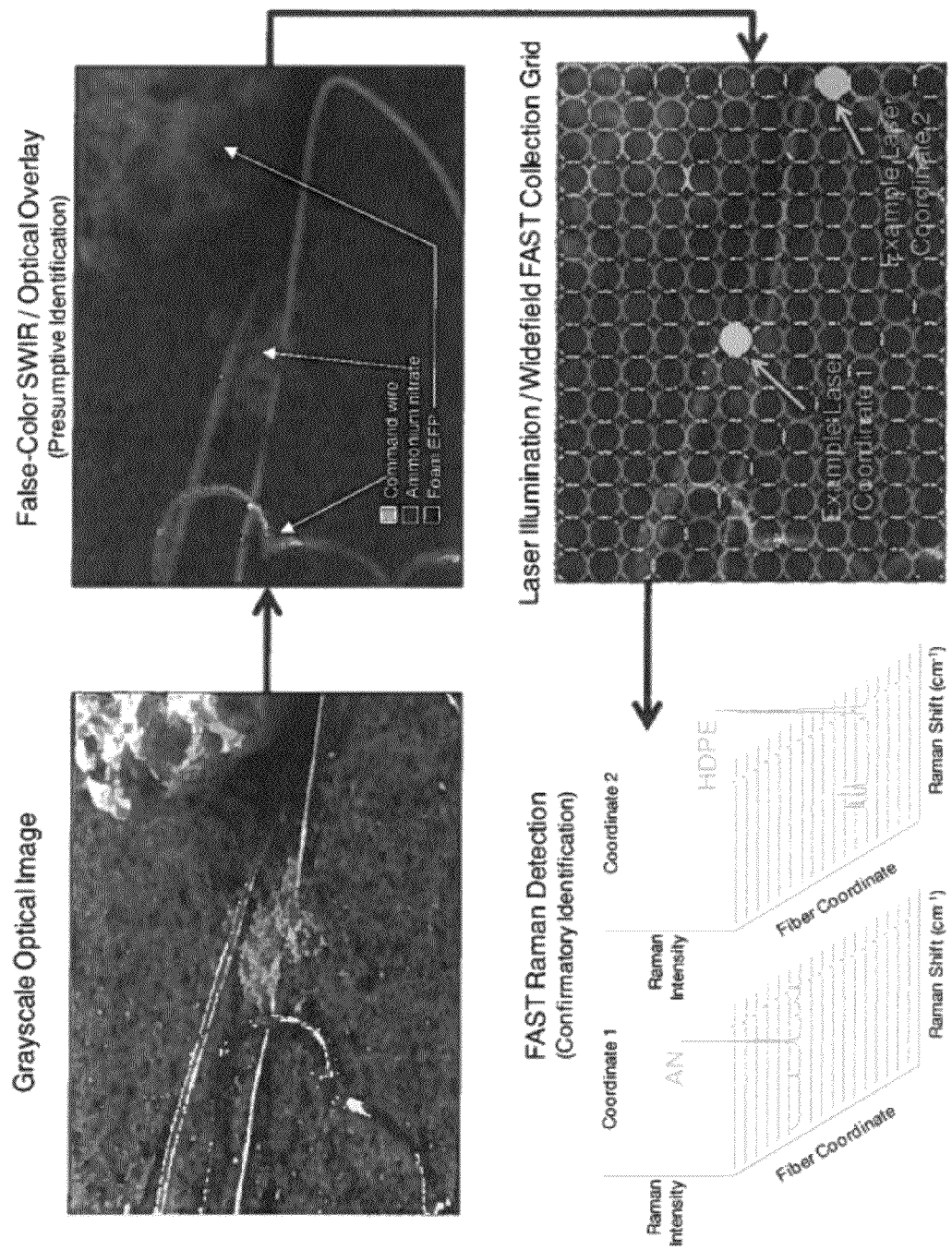
FIG. 13 is illustrative of the operation of the system and method of the present disclosure.

With the detection FAST array aligned to the SWIR hyperspectral FOV, Raman interrogation of the areas determined from the SWIR hyperspectral data can be done through the ALS process: moving the laser spot to those areas and collecting the FAST spectral data set. FIG. 13 illustrates a concept of operation of a system of the present disclosure. As illustrated in FIG. 13, false-color (or "pseudo color") overlays may be applied to images. A more detailed methodology of such a technique is more fully described in U.S. patent application Ser. No. 12/799,779, filed on Apr. 30, 2010, entitled "System and Method for Component Discrimination Enhancement Based on Multispectral Addition Imaging", which is hereby incorporated by reference in its entirety.

Although the disclosure is described using illustrative embodiments provided herein, it should be understood that the principles of the disclosure are not limited thereto and may include modification thereto and permutations thereof.

What is claimed is:

1. A method comprising: illuminating a target area comprising at least one unknown sample to thereby generate a plurality of first interacted photons wherein said first interacted photons are selected from the group consisting of: photons absorbed by said target area, photons reflected by said target area, photons scattered by said target area, photons emitted by said target area, and combinations thereof; assessing said plurality of first interacted photons using a spectroscopic device wherein said assessing comprises obtaining a test SWIR data set representative of said target area; analyzing said test SWIR data set to thereby identify an area of interest in said target area; illuminating said area of interest using a laser light source to thereby generate a plurality of second interacted photons wherein said second interacted photons are selected from the group consisting of: photons absorbed by said area of interest, photons reflected by said area of interest, photons scattered by said area of interest, photons emitted by said area of interest, and combinations thereof; assessing said plurality of second interacted photons using a spectroscopic device wherein said assessing comprises obtaining a test Raman data set representative of said area of interest; analyzing said test Raman data set to thereby identify said area of interest as comprising at least one of: an explosive material, a concealment material, a formulation additive of an explosive material, a binder of an explosive material, a non-explosive material, and combinations thereof.

2. The method of claim 1 further comprising surveying a sample scene using a video capture device to thereby identify a target area based on at least one of size of said target area, shape of said target area, color of said target area, and combinations thereof.

3. The method of claim 1 wherein said analyzing of said test SWIR data set comprises searching a reference SWIR database in accordance with the test SWIR data set in order to identify a known SWIR data set from said reference SWIR database, wherein said reference SWIR database contains a plurality of known SWIR data sets, and wherein each known SWIR data set is associated with a known material.

4. The method of claim 1 wherein said test SWIR data set comprises at least one of: a plurality of spatially resolved SWIR spectra representative of said target SWIR image representative of said target area, and combinations thereof.

5. The method of claim 1 wherein said test SWIR data set comprises a SWIR hyperspectral image representative of said target area wherein said SWIR hyperspectral image comprises an image and a fully resolved spectrum unique to the material for each pixel location in said image.

6. The method of claim 5 wherein said image comprises a spatially accurate wavelength resolved image.

7. The method of claim wherein said analyzing of said test Raman data set comprises searching a reference Raman database in accordance with the test Raman data set in order to identify a known Raman data set from said reference Raman database, wherein said reference Raman database contains a plurality of known Raman data sets, and wherein each know Raman data set is associated with a known material.

8. The method of claim 1 wherein said test Raman data set comprises at least one of: a plurality of spatially resolved Raman spectra representative of an area of interest and a Raman image representative of said area of interest.

9. The method of claim 1 wherein said target area is illuminated using solar radiation.

10. The method of claim 1 further comprising passing said second interacted photons through a fiber array spectral translator device.

11. The method of claim 1 further comprising passing at least one of said first interacted photons and said second interacted photons through a filter wherein said filter is selected from the group consisting of: a multi-conjugate tunable filter, a liquid crystal tunable filter, acousto-optical tunable filters, Lyot liquid crystal tunable filter, Evans Split-Element liquid crystal tunable filter, Solc liquid crystal tunable filter, Ferroelectric liquid crystal tunable filter, Fabry Perot liquid crystal tunable filter, and combinations thereof.

12. The method of claim 1 wherein said area of interest is illuminated using pulsed laser excitation.

13. The method of claim 1 wherein said second interacted photons are assessed using time gated detection.

14. The method of claim 1 further comprising applying a fusion algorithm to at least one of said Raman data set, said SWIR data set, and combinations thereof.

15. The method of claim 1 wherein at least one of said test SWIR data set and said test Raman data set comprises a dynamic chemical image.

16. A system comprising: a first two-dimensional array of detection elements; a laser light source configured to illuminate an area of interest in a target area; a second two-dimensional array of detection elements; a first optical system coupled to said laser light source to direct light to said area of interest; a second optical system wherein said second optical system: collects a first plurality of interacted photons wherein said first plurality of interacted photons are generated by illuminating a target area, directs said first plurality of interacted photons to a first two-dimensional array of detection elements to thereby generate at least one of: a plurality of spatially resolved SWIR spectra representative of said target area, a SWIR image representative of said target area, and combinations thereof, collects a second plurality of interacted photons wherein said second plurality of interacted photons are generated by illuminating an area of interest in said target area with said laser light source, and directing said second plurality of interacted photons to a fiber array spectral translator device, wherein said fiber array spectral translator device comprises: a two-dimensional array of optical fibers drawn into a one-dimensional fiber stack so as to effectively convert a two-dimensional field of view into a curvilinear field of view; a spectrometer coupled to said one-dimensional fiber stack of said fiber array spectral translator device, wherein an entrance slit of the spectrometer is coupled to said one-dimensional fiber stack to generate a plurality of spatially resolved Raman spectra; and wherein said second two-dimensional array of detection elements coupled to said spectrometer detects said spatially resolved Raman spectra to thereby generate at least one of: a plurality of spatially resolved Raman spectra representative of said area of interest and a Raman image representative of said area of interest.

17. The system of claim 16 further comprising a filter for sequentially filtering at least one of said first plurality of interacted photons and said second plurality of interacted photons in each of a plurality of predetermined wavelength bands.

18. The system of claim 17 wherein said filter is a filter selected from the group consisting of: a multi-conjugate tunable filter, a liquid crystal tunable filter, acousto-optical tunable filters, Lyot liquid crystal tunable filter, Evans Split-Element liquid crystal tunable filter, Solc liquid crystal tunable filter, Ferroelectric liquid crystal tunable filter, Fabry Perot liquid crystal tunable filter, and combinations thereof.

19. The system of claim 16 wherein said laser light source comprises a Nd:YLF laser.

20. The system of claim 16 further comprising a telescope used to locate and focus on at least one of a sample scene, the target area, the area of interest, and combinations thereof, and wherein said telescope is coupled to at least one of: said first two-dimensional array of detection elements and said second two-dimensional array of detection elements.

21. The system of claim 16 further comprising: instructions executable by at least one processor that apply a fusion algorithm to one or more of: a plurality of spatially resolved SWIR spectra, a plurality of spatially resolved Raman spectra, and combinations thereof.

22. The system of claim 16 further comprising a video capture device that outputs a dynamic image of at least one of: a the sample scene, the target area, the area of interest, and combinations thereof.

23. The system of claim 16 wherein said laser light source is configured for pulsed laser excitation of said area of interest and said second two-dimensional array of detection elements are configured for time-gated detection of said second plurality of interacted photons.

24. The system of claim 16 wherein said system is configured to operate in one or more of the following modalities: a static modality, an on-the-move modality, a standoff modality, an unmanned ground vehicle modality, and combinations thereof.

25. A method comprising: illuminating a target area comprising at least one unknown sample to thereby generate a plurality of first interacted photons wherein said first interacted photons are selected from the group consisting of: photons absorbed by said target area, photons reflected by said target area, photons scattered by said target area, photons emitted by said target area, and combinations thereof; assessing said first interacted photons to thereby generate a SWIR hyperspectral image representative of said target area; analyzing said SWIR hyperspectral image representative of said target area to thereby identify an area f interest; illuminating said area of interest to thereby generate a plurality of second interacted photons wherein said second interacted photons are selected from the group consisting of photons absorbed by said area of interest, photons reflected by said area of interest, photons scattered by said area of interest, photons emitted by said area of interest, and combinations thereof; assessing said second interacted photons to thereby generate a plurality of spatially resolved Raman spectra representative of said area of interest; analyzing said Raman spectra to thereby identify said area of interest comprising at least one of: an explosive material, a concealment material, a formulation additive of an explosive material, a binder of an explosive material, a non-explosive material, and combinations thereof.

26. The method of claim 25 wherein said target area is illuminated using a solar radiation source.

27. The method of claim 25 wherein said area of interest is illuminated using a laser light source.

28. The method of claim 25 further comprising passing at least one of said first interacted photons and said second interacted photons through a filter, wherein said filter is selected from the group consisting of: a multi-conjugate tunable filter, a liquid crystal tunable filter, acousto-optical tunable filters, Lyot liquid crystal tunable filter, Evans Split-Element liquid crystal tunable filter, Solc liquid crystal tunable filter, Ferroelectric liquid crystal tunable filter, Fabry Perot liquid crystal tunable filter, and combinations thereof.

29. The method of claim 25 further comprising passing said second interacted photons through a fiber array spectral translator device.

30. The method of claim 25 further comprising fusing the results of said analyzing said SWIR image and said analyzing said Raman spectra.

31. The method of claim 25 wherein said SWIR hyperspectral image comprises an image and a fully resolved spectrum unique to the material for each pixel location in said image.

32. The method of claim 25 wherein said area of interest is illuminated using pulsed laser excitation.

33. The method of claim 25 wherein said second interacted photons are assessed using time-gated detection.

34. The method of claim 25 further comprising generating a dynamic chemical image of at least one of: a target area, an area of interest, and combinations thereof.

* * * * *

UNITED STATES PATENT AND TRADEMARK OFFICE
Certificate

Patent No. 8,379,193 B2                                                                               Patented: February 19, 2013

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Charles W. Gardner, Jr., Gibsonia, PA (US); Matthew Nelson, Harrison City, PA (US); and Patrick Treado, Pittsburgh, PA (US).

Signed and Sealed this Seventh Day of January 2014.

GREGORY J. TOATLEY
Supervisory Patent Examiner
Art Unit 2877
Technology Center 2800